(12) United States Patent
Jensen (10) Patent No.: US 7,481,794 B2
(45) Date of Patent: Jan. 27, 2009

(54) COVER

(75) Inventor: Søren Jensen, Lynge (DK)

(73) Assignee: Unomedical A/S, Birkeroed (DK)

( * ) Notice: Subject to any disclaimer, the term of this patent is extended or adjusted under 35 U.S.C. 154(b) by 0 days.

(21) Appl. No.: 11/223,467

(22) Filed: Sep. 9, 2005

(65) Prior Publication Data

US 2006/0041224 A1 Feb. 23, 2006

Related U.S. Application Data

(63) Continuation of application No. 10/366,453, filed on Feb. 12, 2003, now abandoned.

(51) Int. Cl.
*A61M 5/178* (2006.01)

(52) U.S. Cl. .................................. 604/164.08

(58) Field of Classification Search .............. 604/890.1, 604/93.01, 164.08, 171, 174, 180, 192, 198, 604/263, 264

See application file for complete search history.

(56) References Cited

U.S. PATENT DOCUMENTS

| | | | |
|---|---|---|---|
| 643,544 A | 2/1900 | Simmons | |
| 1,838,825 A | 12/1931 | Goldstein | |
| 1,991,103 A | 2/1935 | King | |
| 2,047,010 A | 7/1936 | Dickinson | |
| 2,295,849 A | 9/1942 | Kayden | |
| 2,319,731 A | 5/1943 | Garrett | |
| 2,533,731 A | 12/1950 | Gomberg | |
| 2,630,803 A | 3/1953 | Baran | |
| 2,690,529 A | 9/1954 | Lindblad | |
| 2,730,099 A | 1/1956 | Sullivan | |
| 2,839,060 A | 6/1958 | Ormo | |
| 2,936,141 A | 5/1960 | Rapata | |
| 2,952,420 A | 9/1960 | Von Hoorn | |
| 3,055,361 A | 9/1962 | Ballard | |
| 3,074,541 A | 1/1963 | Roehr | |
| 3,107,785 A | 10/1963 | Roehr | |
| 3,154,080 A | 10/1964 | Rowan et al. | |
| 3,317,166 A | 5/1967 | Janssen | |
| 3,545,286 A | 12/1970 | Stenstrom | |
| 3,610,240 A | 10/1971 | Harautuneian | |
| 3,648,999 A | 3/1972 | Bauer | |
| 3,783,996 A | 1/1974 | Gerard et al. | |
| 3,814,097 A | 6/1974 | Ganderton et al. | |
| 3,831,729 A | 8/1974 | Howard | |
| 3,840,011 A | 10/1974 | Wright | |

(Continued)

FOREIGN PATENT DOCUMENTS

DE 893 296 12/1953

(Continued)

*Primary Examiner*—Kevin C Sirmons
*Assistant Examiner*—Andrew M Gilbert
(74) *Attorney, Agent, or Firm*—Brinks Hofer Gilson & Lione (57) ABSTRACT

A cover (101) for being located on an infusion device, which cover (101) comprises an upper plate element (103) with an upper face (104) and a lower face (105) oriented towards the upper face of the infusion device, wherein the lower face (105) of the plate element (103) comprises attachment means (106), which means cooperate with elements on the infusion device.

Hereby the risk of bacteria and soil collected thereon penetrating into the construction, is reduced considerably, and likewise the cover yields a smoother surface with an ensuing minimisation of the risk of the infusion device being torn off.

21 Claims, 9 Drawing Sheets

U.S. PATENT DOCUMENTS

| | | | |
|---|---|---|---|
| 3,865,236 A | 2/1975 | Rycroft | |
| 3,942,528 A | 3/1976 | Loeser | |
| 3,986,508 A | 10/1976 | Barrington | |
| 4,014,328 A | 3/1977 | Cluff et al. | |
| 4,022,205 A | 5/1977 | Tenczar | |
| 4,146,113 A | 3/1979 | Gavel | |
| 4,150,798 A | 4/1979 | Aragon | |
| 4,188,950 A | 2/1980 | Wardlaw | |
| 4,201,406 A | 5/1980 | Dennehey et al. | |
| 4,227,528 A | 10/1980 | Wardlaw | |
| 4,267,836 A | 5/1981 | Whitney et al. | |
| 4,306,705 A | 12/1981 | Svenson | |
| 4,315,505 A | 2/1982 | Crandall et al. | |
| 4,334,551 A | 6/1982 | Pfister | |
| D267,199 S | 12/1982 | Koenig | |
| 4,365,630 A | 12/1982 | McFlarlane | |
| 4,400,861 A | 8/1983 | Parker | |
| 4,406,042 A | 9/1983 | McPhee | |
| 4,458,344 A | 7/1984 | Coogler | |
| 4,472,024 A | 9/1984 | Konomura et al. | |
| 4,473,369 A | 9/1984 | Lueders et al. | |
| 4,500,312 A | 2/1985 | McFarlane | |
| 4,517,971 A | 5/1985 | Sorbonned | |
| 4,530,695 A | 7/1985 | Phillips et al. | |
| 4,531,686 A | 7/1985 | Shaw | |
| 4,576,846 A | 3/1986 | Noel | |
| 4,606,735 A | 8/1986 | Wilder et al. | |
| 4,610,469 A | 9/1986 | Wolff-Mooij | |
| 4,616,790 A | 10/1986 | Beltran | |
| 4,619,349 A | 10/1986 | Braun | |
| 4,635,683 A | 1/1987 | Nielsen | |
| 4,637,404 A | 1/1987 | Gessman | |
| 4,662,873 A | 5/1987 | Lash et al. | |
| 4,682,702 A | 7/1987 | Gach | |
| 4,713,059 A | 12/1987 | Bickelhaupt et al. | |
| 4,734,092 A | 3/1988 | Millerd | |
| 4,755,173 A | 7/1988 | Konopka et al. | |
| 4,758,020 A | 7/1988 | Boyd | |
| 4,800,629 A | 1/1989 | Ikeda | |
| 4,802,638 A | 2/1989 | Burger et al. | |
| 4,817,603 A | 4/1989 | Turner et al. | |
| RE32,922 E | 5/1989 | Levin et al. | |
| 4,838,871 A | 6/1989 | Luther | |
| 4,840,613 A | 6/1989 | Balbierz | |
| 4,850,974 A | 7/1989 | Bickelhaupt et al. | |
| 4,878,897 A | 11/1989 | Katzin | |
| 4,895,570 A | 1/1990 | Larkin | |
| D306,500 S | 3/1990 | Brahler | |
| 4,913,369 A | 4/1990 | Lia et al. | |
| 4,917,669 A | 4/1990 | Bonaldo | |
| 4,935,010 A | 6/1990 | Cox et al. | |
| 4,950,163 A | 8/1990 | Zimble | |
| 4,950,252 A | 8/1990 | Luther et al. | |
| 4,978,338 A | 12/1990 | Melsky et al. | |
| 4,982,842 A | 1/1991 | Hollister | |
| 4,986,817 A | 1/1991 | Code | |
| 4,994,045 A | 2/1991 | Ranford | |
| 5,011,475 A | 4/1991 | Olson | |
| 5,024,662 A | 6/1991 | Menes et al. | |
| 5,067,496 A | 11/1991 | Eisele | |
| 5,077,872 A | 1/1992 | Guthammar | |
| 5,083,757 A | 1/1992 | Barsky | |
| 5,098,389 A | 3/1992 | Cappucci | |
| 5,112,313 A | 5/1992 | Sallee | |
| 5,116,319 A | 5/1992 | Van den Haak | |
| 5,116,324 A | 5/1992 | Brierley et al. | |
| 5,116,325 A | 5/1992 | Paterson | |
| 5,121,751 A | 6/1992 | Panalletta | |
| 5,134,593 A | 7/1992 | Logan et al. | |
| 5,134,594 A | 7/1992 | Woo | |
| 5,137,524 A | 8/1992 | Lynn et al. | |
| 5,141,496 A | 8/1992 | Dalto et al. | |
| 5,147,319 A | 9/1992 | Ishikawa et al. | |
| 5,147,375 A | 9/1992 | Sullivan et al. | |
| 5,161,681 A | 11/1992 | Kemp et al. | |
| 5,163,915 A | 11/1992 | Holleron | |
| 5,176,662 A | 1/1993 | Bartholomew et al. | |
| 5,188,314 A | 2/1993 | Peters | |
| 5,188,611 A | 2/1993 | Orgain | |
| RE34,223 E | 4/1993 | Bonaldo | |
| 5,222,947 A | 6/1993 | D'Amico | |
| 5,232,454 A | 8/1993 | Hollister | |
| 5,236,143 A | 8/1993 | Dragon | |
| 5,240,199 A | 8/1993 | Peters | |
| 5,248,301 A | 9/1993 | Koenig et al. | |
| 5,256,152 A | 10/1993 | Marks | |
| 5,257,980 A | 11/1993 | Van Antwerp et al. | |
| 5,265,822 A | 11/1993 | Shober, Jr. et al. | |
| 5,269,799 A | 12/1993 | Daniel | |
| 5,279,579 A | 1/1994 | D'Amico | |
| 5,279,591 A | 1/1994 | Simon | |
| 5,282,793 A | 2/1994 | Larson | |
| 5,300,030 A | 4/1994 | Crossman et al. | |
| 5,312,359 A | 5/1994 | Wallace | |
| 5,312,369 A | 5/1994 | Arcusin et al. | |
| 5,316,246 A | 5/1994 | Scott et al. | |
| 5,324,302 A | 6/1994 | Crouse | |
| 5,342,319 A | 8/1994 | Watson et al. | |
| 5,342,324 A | 8/1994 | Tucker | |
| 5,343,637 A | 9/1994 | Schindler | |
| 5,350,392 A | 9/1994 | Purcell et al. | |
| 5,354,280 A | 10/1994 | Haber et al. | |
| 5,366,469 A | 11/1994 | Steg et al. | |
| 5,372,592 A | 12/1994 | Gambale | |
| 5,376,082 A | 12/1994 | Phelps | |
| 5,380,067 A | 1/1995 | Turvill et al. | |
| 5,384,174 A | 1/1995 | Ward et al. | |
| 5,387,197 A | 2/1995 | Smith et al. | |
| 5,388,931 A | 2/1995 | Carlson | |
| 5,390,669 A | 2/1995 | Stuart et al. | |
| 5,391,151 A | 2/1995 | Wilmot | |
| 5,403,288 A | 4/1995 | Stanners | |
| 5,405,332 A | 4/1995 | Opalek | |
| 5,429,607 A | 7/1995 | McPhee | |
| 5,429,613 A | 7/1995 | D'Amico | |
| 5,433,307 A | 7/1995 | Jeppe | |
| D362,718 S | 9/1995 | Deily et al. | |
| 5,449,349 A | 9/1995 | Sallee et al. | |
| 5,487,506 A | 1/1996 | Drummond et al. | |
| 5,490,841 A | 2/1996 | Landis | |
| 5,492,313 A | 2/1996 | Pan et al. | |
| 5,505,709 A | 4/1996 | Funderburk et al. | |
| 5,507,730 A | 4/1996 | Haber et al. | |
| 5,519,167 A | 5/1996 | Kunimoto et al. | |
| 5,520,654 A | 5/1996 | Wahlberg | |
| 5,522,803 A | 6/1996 | Teissen-Simony | |
| 5,533,974 A | 7/1996 | Gaba | |
| 5,540,709 A | 7/1996 | Ramel | |
| 5,545,143 A | 8/1996 | Fischell | |
| 5,545,152 A | 8/1996 | Funderburk et al. | |
| 5,554,130 A | 9/1996 | McDonald et al. | |
| 5,558,650 A | 9/1996 | McPhee | |
| 5,562,636 A | 10/1996 | Utterberg | |
| 5,584,813 A | 12/1996 | Livingston et al. | |
| 5,591,188 A | 1/1997 | Waisman | |
| 5,599,309 A | 2/1997 | Marshall et al. | |
| 5,599,315 A | 2/1997 | McPhee | |
| 5,599,318 A | 2/1997 | Sweeney et al. | |
| 5,628,765 A | 5/1997 | Morita | |
| 5,643,214 A | 7/1997 | Marshall | |
| 5,643,216 A | 7/1997 | White | |
| 5,643,220 A | 7/1997 | Cosme | |
| 5,662,617 A | 9/1997 | Odell et al. | |
| 5,665,071 A | 9/1997 | Wyrick | |

| | | | | | | |
|---|---|---|---|---|---|---|
| 5,665,075 | A | 9/1997 | Gyure et al. | 6,579,267 B2 * | 6/2003 | Lynch et al. |
| 5,681,323 | A | 10/1997 | Arick | 6,582,397 B2 | 6/2003 | Alesi et al. |
| 5,695,476 | A | 12/1997 | Harris | 6,595,962 B1 * | 7/2003 | Perthu |
| 5,704,920 | A | 1/1998 | Gyure | 6,607,509 B2 * | 8/2003 | Bobroff et al. |
| 5,709,516 | A | 1/1998 | Peterson et al. | 6,629,949 B1 * | 10/2003 | Douglas |
| 5,714,225 | A | 2/1998 | Hansen et al. | 6,645,182 B1 | 11/2003 | Szabo |
| 5,741,288 | A | 4/1998 | Rife | 6,685,674 B2 | 2/2004 | Douglas et al. |
| 5,752,923 | A | 5/1998 | Terwilliger | 6,702,779 B2 | 3/2004 | Connelly et al. |
| 5,810,835 | A | 9/1998 | Ryan et al. | 6,726,649 B2 * | 4/2004 | Swenson et al. |
| 5,820,598 | A | 10/1998 | Gazza et al. | 6,736,797 B1 | 5/2004 | Larsen et al. |
| D402,538 | S | 12/1998 | Wagter et al. | 6,749,589 B1 | 6/2004 | Douglas et al. |
| 5,843,001 | A | 12/1998 | Goldenberg | 6,790,199 B1 | 9/2004 | Gianakos |
| 5,851,197 | A * | 12/1998 | Marano et al. ............ 604/135 | 6,805,686 B1 | 10/2004 | Fathallah et al. |
| 5,858,001 | A | 1/1999 | Tsals et al. | 6,811,545 B2 * | 11/2004 | Vaillancourt |
| 5,865,806 | A | 2/1999 | Howell | 6,814,720 B2 | 11/2004 | Olsen et al. |
| 5,873,540 | A | 2/1999 | Hardin | 6,824,530 B2 | 11/2004 | Wagner et al. |
| 5,899,886 | A | 5/1999 | Cosme | 6,824,531 B1 | 11/2004 | Zecha, Jr. et al. |
| 5,913,846 | A | 6/1999 | Szabo | 6,830,562 B2 | 12/2004 | Mogensen et al. |
| 5,915,640 | A | 6/1999 | Wagter et al. | 6,837,877 B2 | 1/2005 | Zurcher |
| 5,919,167 | A | 7/1999 | Mulhauser et al. | 6,840,922 B2 | 1/2005 | Nielsen et al. |
| 5,925,032 | A | 7/1999 | Clements | 6,880,701 B2 | 4/2005 | Bergeron et al. |
| 5,947,935 | A | 9/1999 | Rinehart et al. | 6,916,017 B2 | 7/2005 | Noe |
| 5,951,523 | A | 9/1999 | Osterlind et al. | 6,923,791 B2 * | 8/2005 | Douglas ............... 604/167.05 |
| 5,954,643 | A | 9/1999 | VanAntwerp et al. | 6,926,694 B2 | 8/2005 | Marano-Ford et al. |
| 5,957,892 | A | 9/1999 | Thorne | 6,939,331 B2 | 9/2005 | Ohshima |
| 5,968,011 | A * | 10/1999 | Larsen et al. ......... 604/288.02 | 6,949,084 B2 | 9/2005 | Marggi et al. |
| 5,975,120 | A | 11/1999 | Novosel | 2001/0004970 A1 | 6/2001 | Hollister et al. |
| 5,980,488 | A | 11/1999 | Thorne | 2001/0016714 A1 | 8/2001 | Bell et al. |
| 5,980,506 | A | 11/1999 | Mathiasen | 2001/0021827 A1 | 9/2001 | Ferguson et al. |
| 5,984,224 | A | 11/1999 | Yang | 2001/0039401 A1 | 11/2001 | Ferguson et al. |
| 5,984,897 | A | 11/1999 | Peterson et al. | 2001/0041875 A1 | 11/2001 | Higuchi et al. |
| 5,992,787 | A | 11/1999 | Burke | 2002/0022855 A1 | 2/2002 | Bobroff et al. |
| D417,733 | S | 12/1999 | Howell et al. | 2002/0068904 A1 | 6/2002 | Bierman et al. |
| 6,017,328 | A | 1/2000 | Fischell et al. | 2002/0072720 A1 | 6/2002 | Hague et al. |
| D421,119 | S | 2/2000 | Musgrave et al. | 2002/0077599 A1 | 6/2002 | Wojcik |
| 6,039,629 | A | 3/2000 | Mitchell | 2002/0107489 A1 | 8/2002 | Lee |
| 6,042,570 | A | 3/2000 | Bell et al. | 2002/0111581 A1 | 8/2002 | Sasso |
| 6,045,533 | A | 4/2000 | Kriesel et al. | 2002/0145073 A1 | 10/2002 | Swanson |
| 6,050,976 | A | 4/2000 | Thorne et al. | 2002/0156424 A1 | 10/2002 | Suzuki et al. |
| 6,056,718 | A | 5/2000 | Funderburk et al. | 2002/0156427 A1 | 10/2002 | Suzuki et al. |
| 6,074,371 | A | 6/2000 | Fischell | 2002/0161332 A1 * | 10/2002 | Ramey .................. 604/164.07 |
| 6,086,008 | A | 7/2000 | Gray et al. | 2002/0169419 A1 | 11/2002 | Steg |
| 6,086,575 | A | 7/2000 | Mejslov | 2002/0173748 A1 | 11/2002 | McConnell et al. |
| 6,090,068 | A | 7/2000 | Chanut | 2002/0183688 A1 | 12/2002 | Lastovich et al. |
| 6,093,172 | A | 7/2000 | Funderburk et al. | 2002/0189688 A1 | 12/2002 | Roorda |
| 6,093,179 | A | 7/2000 | O'Hara et al. | 2002/0193737 A1 | 12/2002 | Popovsky |
| 6,099,503 | A | 8/2000 | Stardella | 2002/0193744 A1 | 12/2002 | Alesi et al. |
| 6,105,218 | A | 8/2000 | Reekie | 2003/0069548 A1 * | 4/2003 | Connelly et al. |
| 6,120,482 | A | 9/2000 | Szabo | 2003/0105430 A1 | 6/2003 | Lavi et al. |
| 6,123,690 | A | 9/2000 | Mejslov | 2003/0109829 A1 | 6/2003 | Mogensen et al. |
| 6,132,755 | A | 10/2000 | Eicher et al. | 2003/0125669 A1 * | 7/2003 | Safabash et al. |
| 6,183,464 | B1 | 2/2001 | Sharp et al. | 2003/0125678 A1 * | 7/2003 | Swenson et al. |
| 6,193,694 | B1 | 2/2001 | Bell et al. | 2003/0130619 A1 * | 7/2003 | Safabash et al. |
| 6,213,979 | B1 * | 4/2001 | Bierman .................. 604/174 | 2003/0139704 A1 * | 7/2003 | Lin |
| 6,219,574 | B1 | 4/2001 | Cormier et al. | 2003/0158520 A1 | 8/2003 | Safabash et al. |
| 6,221,058 | B1 | 4/2001 | Kao et al. | 2003/0176843 A1 * | 9/2003 | Wilkinson |
| 6,248,093 | B1 | 6/2001 | Moberg | 2003/0181863 A1 | 9/2003 | Davis et al. |
| 6,293,925 | B1 | 9/2001 | Safabash et al. | 2003/0181868 A1 * | 9/2003 | Swenson |
| 6,302,866 | B1 | 10/2001 | Marggi | 2003/0181873 A1 * | 9/2003 | Swenson |
| 6,319,232 | B1 | 11/2001 | Kashmer | 2003/0181874 A1 | 9/2003 | Bressler et al. |
| 6,322,535 | B1 | 11/2001 | Hitchins et al. | 2003/0187394 A1 * | 10/2003 | Wilkinson et al. |
| 6,322,808 | B1 | 11/2001 | Trautman et al. | 2003/0187395 A1 * | 10/2003 | Gabel et al. ................. 604/134 |
| 6,334,856 | B1 | 1/2002 | Allen et al. | 2003/0199823 A1 * | 10/2003 | Bobroff et al. |
| 6,355,021 | B1 | 3/2002 | Nielsen et al. | 2003/0216686 A1 | 11/2003 | Lynch et al. |
| 6,379,335 | B1 | 4/2002 | Rigon et al. | 2003/0225373 A1 * | 12/2003 | Bobroff et al. |
| D456,692 | S | 5/2002 | Epstein | 2003/0225374 A1 | 12/2003 | Mathiasen |
| 6,387,076 | B1 | 5/2002 | Landuyt | 2003/0229308 A1 | 12/2003 | Tsals et al. |
| 6,488,663 | B1 | 12/2002 | Steg | 2003/0229316 A1 * | 12/2003 | Hwang et al. |
| 6,517,517 | B1 | 2/2003 | Farrugia et al. | 2004/0002682 A1 * | 1/2004 | Kovelman et al. |
| 6,520,938 | B1 * | 2/2003 | Funderburk et al. .... 604/164.08 | 2004/0006316 A1 | 1/2004 | Patton |
| D472,316 | S | 3/2003 | Douglas et al. | 2004/0026840 A1 | 2/2004 | Eckel et al. |
| D472,630 | S * | 4/2003 | Douglas et al. | 2004/0044306 A1 * | 3/2004 | Lynch et al. |
| 6,572,586 | B1 * | 6/2003 | Wojcik ................... 604/165.01 | 2004/0049159 A1 * | 3/2004 | Barrus et al. |

| | | | | | | |
|---|---|---|---|---|---|---|
| 2004/0068231 A1* | 4/2004 | Blondeau | EP | 0 916 361 A1 | 5/1999 | |
| 2004/0087913 A1* | 5/2004 | Rogers et al. | EP | 0 931 560 A1 | 7/1999 | |
| 2004/0111068 A1* | 6/2004 | Swenson | EP | 0 956 879 A1 | 11/1999 | |
| 2004/0112781 A1* | 6/2004 | Hofverberg et al. | EP | 1 045 145 A1 | 10/2000 | |
| 2004/0116865 A1 | 6/2004 | Bengtsson | EP | 1 060 757 A1 | 12/2000 | |
| 2004/0138612 A1 | 7/2004 | Shermer et al. | EP | 1 086 718 A | 3/2001 | |
| 2004/0138620 A1* | 7/2004 | Douglas et al. | EP | 1 125 593 A1 | 8/2001 | |
| 2004/0143216 A1 | 7/2004 | Douglas et al. | EP | 1 167 765 A2 | 1/2002 | |
| 2004/0143218 A1* | 7/2004 | Das | EP | 0 775 501 | 6/2002 | |
| 2004/0158202 A1* | 8/2004 | Jensen | EP | 0 894 216 B1 | 7/2003 | |
| 2004/0158207 A1 | 8/2004 | Hunn et al. | EP | 1 380 315 A1 | 1/2004 | |
| 2004/0162518 A1 | 8/2004 | Connelly et al. | EP | 0 956 879 A1 | 7/2004 | |
| 2004/0171989 A1* | 9/2004 | Horner et al. | FR | 576 849 | 8/1924 | |
| 2004/0178098 A1* | 9/2004 | Swenson et al. | FR | 576849 | 8/1924 | |
| 2004/0186446 A1* | 9/2004 | Ohshima | FR | 2 611 013 | 8/1988 | |
| 2004/0199123 A1 | 10/2004 | Nielsen | FR | 2725902 | 10/1994 | |
| 2004/0204687 A1* | 10/2004 | Mogensen et al. | FR | 2 733 915 | 11/1996 | |
| 2004/0204690 A1 | 10/2004 | Yashiro et al. | FR | 2733915 A1 | 11/1996 | |
| 2004/0220528 A1* | 11/2004 | Garcia, Jr. | FR | 2 781 617 A1 | 1/2000 | |
| 2004/0238392 A1 | 12/2004 | Peterson et al. | FR | 2781617 A1 | 1/2000 | |
| 2004/0243065 A1 | 12/2004 | McConnell et al. | GB | 478803 | 1/1938 | |
| 2004/0254433 A1 | 12/2004 | Bandis et al. | GB | 591730 | 3/1946 | |
| 2004/0260235 A1 | 12/2004 | Douglas | GB | 906574 | 9/1962 | |
| 2004/0260250 A1 | 12/2004 | Harris et al. | GB | 1 268 575 | 3/1972 | |
| 2005/0035014 A1 | 2/2005 | Cane | GB | 1 403 034 | 8/1975 | |
| 2005/0101932 A1 | 5/2005 | Cote et al. | GB | 2 224 808 A | 5/1990 | |
| 2005/0101933 A1 | 5/2005 | Marrs et al. | GB | 2 270 552 A | 3/1994 | |
| 2005/0107743 A1 | 5/2005 | Fangrow, Jr. | JP | 05326062 A | 12/1993 | |
| 2005/0113761 A1 | 5/2005 | Faust et al. | JP | 5326062 A | 12/1993 | |
| 2005/0119637 A1 | 6/2005 | Lundgren et al. | JP | 7051251 | 11/1995 | |
| 2005/0124936 A1 | 6/2005 | Mogensen et al. | JP | 9217584 A | 9/1997 | |
| 2005/0159709 A1 | 7/2005 | Wilkinson | JP | 2000-59877 A | 2/2000 | |
| 2005/0215979 A1 | 9/2005 | Konerup et al. | JP | 3140740 | 2/2000 | |
| 2005/0251098 A1 | 11/2005 | Wyss et al. | JP | 2000059877 A | 2/2000 | |
| 2005/0277892 A1 | 12/2005 | Chen | JP | 3140740 B2 | 3/2001 | |
| 2005/0283114 A1 | 12/2005 | Bresina et al. | JP | 2002-028246 | 1/2002 | |
| 2006/0030815 A1 | 2/2006 | Csincsura et al. | NL | 1017427 C | 11/2002 | |
| | | | WO | WO 87/06474 | 11/1987 | |
| | FOREIGN PATENT DOCUMENTS | | WO | WO 93/03787 | 3/1993 | |
| DE | 1 053 541 | 3/1959 | WO | WO 93/05840 | 4/1993 | |
| DE | 26 20 009 A1 | 12/1977 | WO | WO 94/20160 | 9/1994 | |
| DE | 28 03 509 | 8/1979 | WO | WO 95/28327 A | 10/1995 | |
| DE | 28 03 509 A | 8/1979 | WO | WO 96/35472 A1 | 11/1996 | |
| DE | 37 15 965 A | 1/1988 | WO | WO 98/09065 | 3/1998 | |
| DE | 196 31 921 | 3/1997 | WO | WO 98/58693 | 12/1998 | |
| DE | 298 18 311 U1 | 3/1999 | WO | WO 99/07435 | 2/1999 | |
| DE | 298 18 311 U1 | 11/1999 | WO | WO 99/33504 | 7/1999 | |
| DE | 19847143 A1 | 1/2000 | WO | WO 99/36009 | 7/1999 | |
| DE | 101 06 074 A1 | 9/2000 | WO | WO 99/56802 | 11/1999 | |
| DE | 299 21 406 | 1/2001 | WO | WO 99/61815 | 12/1999 | |
| DE | 101 06 074 A1 | 6/2002 | WO | WO 00/02614 | 1/2000 | |
| DE | 299 21 406 U1 | 11/2002 | WO | WO 00/03757 | 1/2000 | |
| DK | 37 22 893 C1 | 6/1988 | WO | WO 00/44324 A1 | 8/2000 | |
| DK | 38 23 447 | 2/1996 | WO | WO 01/04507 A1 | 1/2001 | |
| DK | 196 10 692 A1 | 9/1997 | WO | WO 01/30419 A2 | 5/2001 | |
| DK | 198 47 143 A1 | 1/2000 | WO | WO 01/68180 | 9/2001 | |
| DK | 100 49 001 A1 | 4/2002 | WO | WO 01/81785 A1 | 11/2001 | |
| EP | 0 188 014 B1 | 10/1985 | WO | WO 01/93926 A2 | 12/2001 | |
| EP | 0 239 244 B1 | 2/1987 | WO | WO 02/46080 | 6/2002 | |
| EP | 0 298 521 B1 | 9/1990 | WO | WO 02/066854 A1 | 8/2002 | |
| EP | 0 184 231 B1 | 1/1992 | WO | WO 02/094352 | 11/2002 | |
| EP | 0 475 857 | 3/1992 | WO | WO 02/100457 | 12/2002 | |
| EP | 0 544 837 B1 | 6/1993 | WO | WO 02/068014 | 1/2003 | |
| EP | 0 633 039 | 7/1994 | WO | WO 03/015860 A1 | 2/2003 | |
| EP | 0 651 662 B1 | 5/1995 | WO | WO 03/026728 | 4/2003 | |
| EP | 0 714 631 B1 | 6/1996 | WO | WO 2004/030726 A | 4/2004 | |
| EP | 744 183 A2 | 11/1996 | WO | WO 2004/087240 | 10/2004 | |
| EP | 0 747 006 A1 | 12/1996 | WO | WO 2005/004973 | 1/2005 | |
| EP | 0 688 232 B1 | 12/1998 | | | | |
| EP | 0 884 108 A1 | 12/1998 | * cited by examiner | | | |

PRIOR ART

Fig. 1

PRIOR ART

Fig. 2

PRIOR ART

Fig. 3

PRIOR ART

COVER

This application is a continuation application of application Ser. No. 10/366,453, filed on Feb. 12, 2003 now abandoned, the entirety of this reference is incorporated herein.

FIELD OF THE INVENTION

The invention relates to a cover for being located on an infusion device, said cover comprising an upper plate element with an upper face and a lower face oriented towards the upper face of the infusion device.

BACKGROUND

In connection with an infusion device being located on the skin, it is known to shield it; such shielding, however, involving a complete covering of the infusion device and in such a manner that it becomes inaccessible to manipulation from the outside.

One example of this is known for instance from WO 87/06474. This discloses a device that can be strapped to the body over the location of insertion of an intravenous needle to shield the puncture area against contact and for anchoring the tube so that the needle will not be pulled out inadvertently.

However the construction necessitates use of an additional frame for securing the infusion device and also for securing the dome that shields the entire infusion device and is also manufactured to be very voluminous. There is thus a risk of it being torn off during use and, likewise, it prevents access to the infusion device and, furthermore, there is a risk of the adhesive effect ceasing and, likewise, it cannot be expected that adjustments of the shielding are possible as the adhesive effect will cease.

BRIEF SUMMARY OF THE INVENTION

It is thus the object of the present invention to provide a cover that remedies the problems that may occur in connection with the prior art covers and whereby complete or partial shielding of the upper free face of the infusion set is enabled, but wherein the lower face is unshielded and the side faces are also partially unshielded, and wherein a shielding of the plate takes place directly on the infusion device. Hereby it is obtained that the risk of bacteria and soil collected thereon penetrating into the construction is reduced considerably, and likewise the cover enables a smoother surface with an ensuing minimisation of the risk of the infusion device being torn off.

This object is obtained by a cover for being located on an infusion device and wherein the lower face of the plate element also comprises attachment means, said means co-operating with elements on the infusion device.

Thus, the cover functions in that, by means of its attachment means that are provided on the lower free face, it fits into the upper face of the infusion device and by a press fitting ensures that the cover is securely attached onto the infusion device due to the clamping effect obtained between the individual attachment means and can be reinforced by the infusion device preferably comprising, as described in the attached claims, a side flange, and wherein this side flange cooperates with the attachment means to bring about a secure attachment of the cover on the infusion device.

Preferably the upper face of the infusion device is configured with recesses, on the one hand longitudinally extending recesses and rather rounded cavities, and consequently the attachment means match these cavities and bring about the attachment. The upper face of the cover is smooth throughout and the entire lower face of the cover is essentially congruent with the upper face of the infusion device, whereby the adaptation is optimised. The cover may be removed by side flanges, if any, being seized thereby exposing the entire infusion device. The cover can be configured such that the upper plate does not cover the entire infusion device, but merely comprises a tongue portion that extends across a portion of the upper face of the infusion device and an essentially partially circular part that covers the remainder.

In one embodiment of the present invention, the cover further comprises a flange that forms a first angle in relation to the upper plate and is connected thereto, in case the infusion device that consists of two parts is separated it is possible—due to the presence of the flange—for the cover to remain in place on the part designated the cannula part; the attachment means and the flange bringing about a squeezing effect that secures the cover in position.

In another embodiment of the present invention, the cover includes a face of the flange facing towards outer side faces of the infusion device that is congruent therewith, thus an optimal complete or partial shielding of the infusion device is obtained.

In yet another embodiment of the present invention, a cover is provided wherein the expanse of the upper plate element is smaller than the expanse of the upper face of the infusion device, and wherein the flange extends partially around the side faces of the infusion device which makes it possible to seize the exposed parts of the infusion device and thus to carry out a separation thereof.

In another embodiment of the present invention, a cover is provided wherein the attachment means are male parts and that the elements on the infusion device are provided by recesses that enable close contact between the cover and the infusion device, and whereby a click-attachment is obtained.

In yet another embodiment of the present invention, a cover is provided wherein the attachment means are male parts and that the elements on the infusion device are provided by recesses, the attachment means further comprise at least two protruding plate elements located at a second mutual distance, and the protruding plate elements comprise rectangular plate-shaped elements extending perpendicularly to the lower face that bring about a convenient shape of the attachment means.

In another embodiment of the present invention, a cover is provided wherein the protruding plate elements comprise a concave delimiting edge and concave side face that enable separation of the hub and cannula part while simultaneously the cover remains in place on the cannula part.

The invention will now be explained in further detail with reference to the drawing wherein

DETAILED DESCRIPTION OF THE INVENTION

Figure 1:
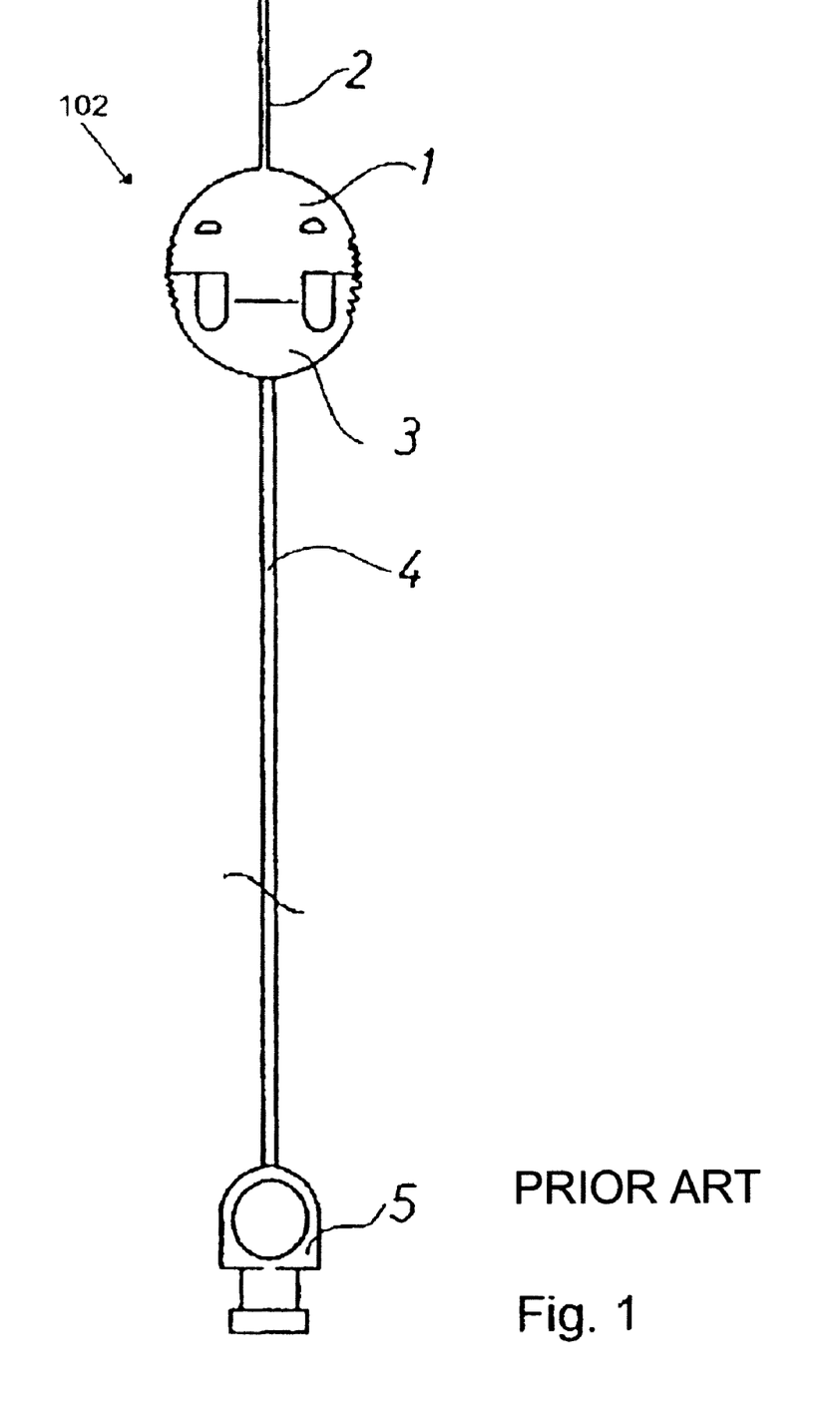
FIGS. 1-4 show an infusion set as described in U.S. Pat. No. 5,522,803 and for which a cover in accordance with the invention can be used.

The infusion set of FIG. 1 comprises a cannula housing 1 with a soft cannula 2 secured therein and manufactured in a conventional manner of a suitable plastics material. The infusion set further comprises a connecting hub 3 connected in a conventional manner through a hose 4 with a lower coupling member 5 to be used for the coupling thereof to an insulin pump (not shown).

Figure 2:
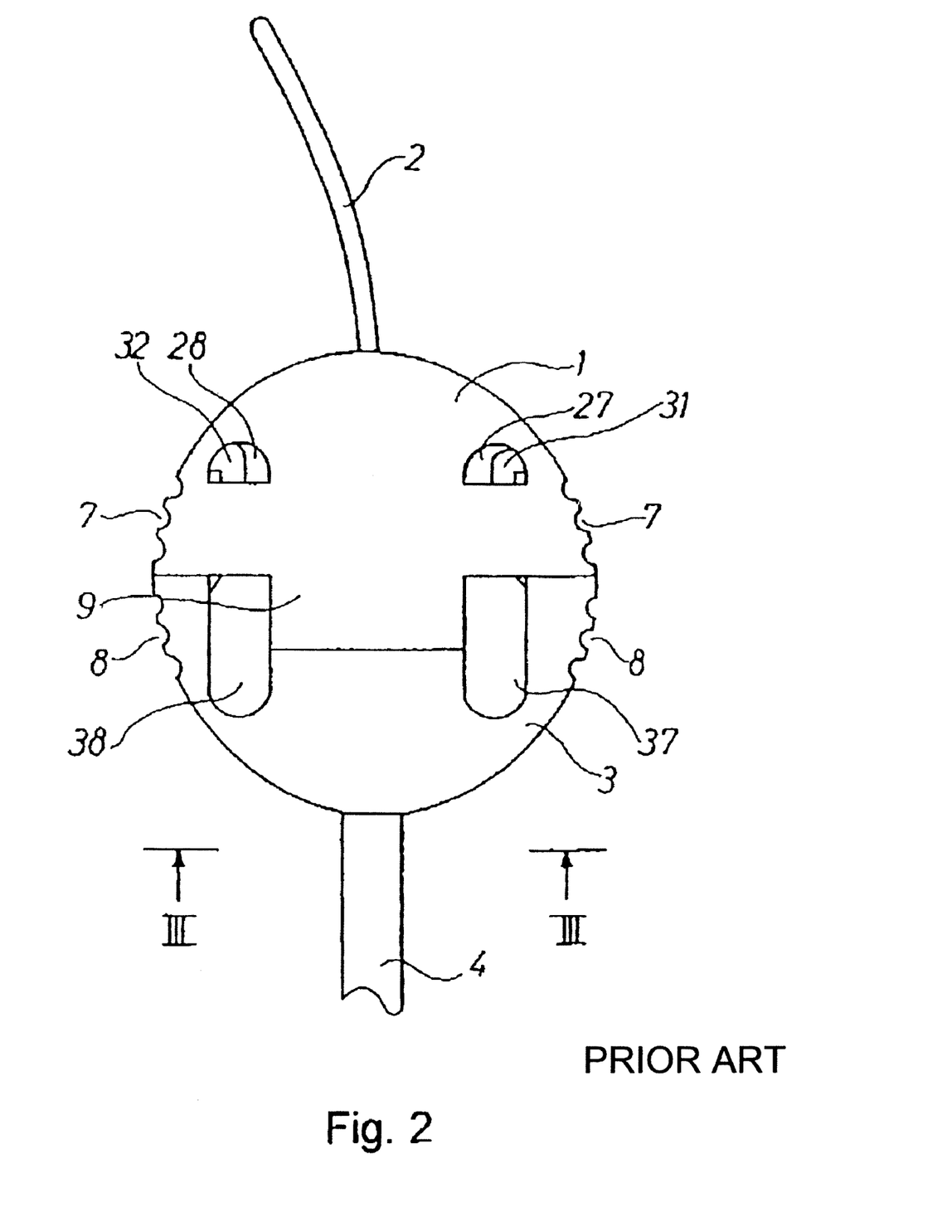
Figure 3:
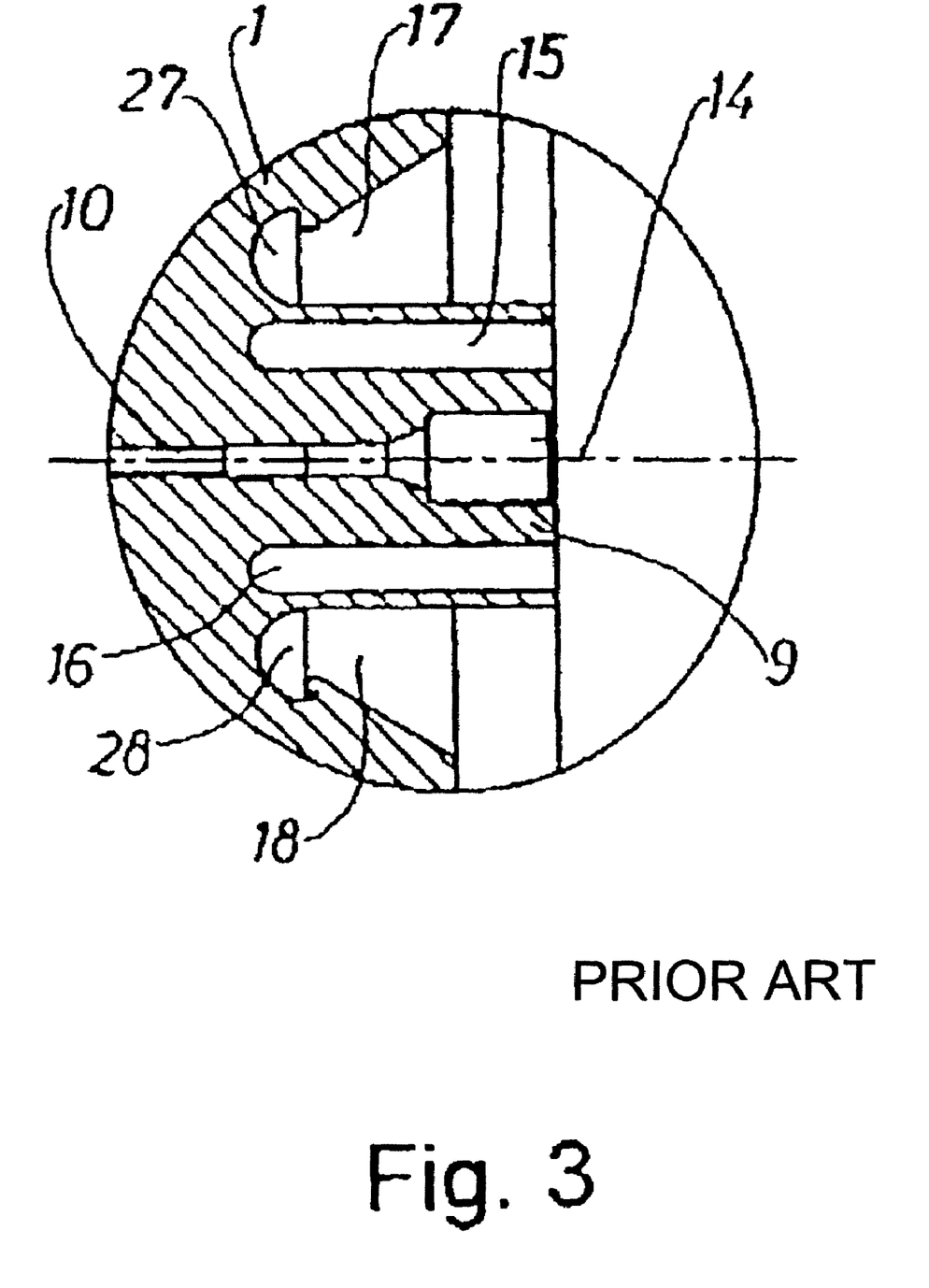

FIG. 2 shoves the cannula housing 1 and the connecting hub 3 on a larger scale and creating the infusion device 102. It appears clearly that together they are of a relatively flat shape and of a uniform thickness and have a substantially plane rear side. When seen from the top, they are together of a substantially circular shape, said shape being interrupted only by recesses 7 and 8, respectively, for facilitating a finger-handling. As illustrated in FIG. 2, the cannula housing 1 and the connecting hub 3 are divided substantially along a diametrical central plane, a central projection 9 being provided on said cannula housing 1 and projecting into a mating recess in the connecting hub 3. In FIG. 3, the cannula 2 is slightly curved in order to illustrate that it is bendable.

As illustrated in FIG. 3, the cannula housing comprises two guide openings 16 and 15 and two locking openings 17 and 18 in addition to the rectilinear through bore 10. These openings are symmetrically shaped about a plane including the central axis 14 of the through passageway 13 and extending perpendicular to the rear side 6. The guide openings 15 and 16 are elongate openings are adapted to receive mating guide pins 21 and 22 on the connecting hub 3, cf. FIG. 4.

The locking openings 17 and 18 adjacent the guide openings 15 and 16 and the central through bore 10 follow a rectilinear course parallel to the central axis 14 and consequently also parallel to the guide openings 15 and 16. The locking openings 17 and 18 at the bottom are connected to the surface of the cannula housing through a shaft or channel 27 and 28, respectively, extending perpendicular from said locking openings 17 and 18.

Figure 4:
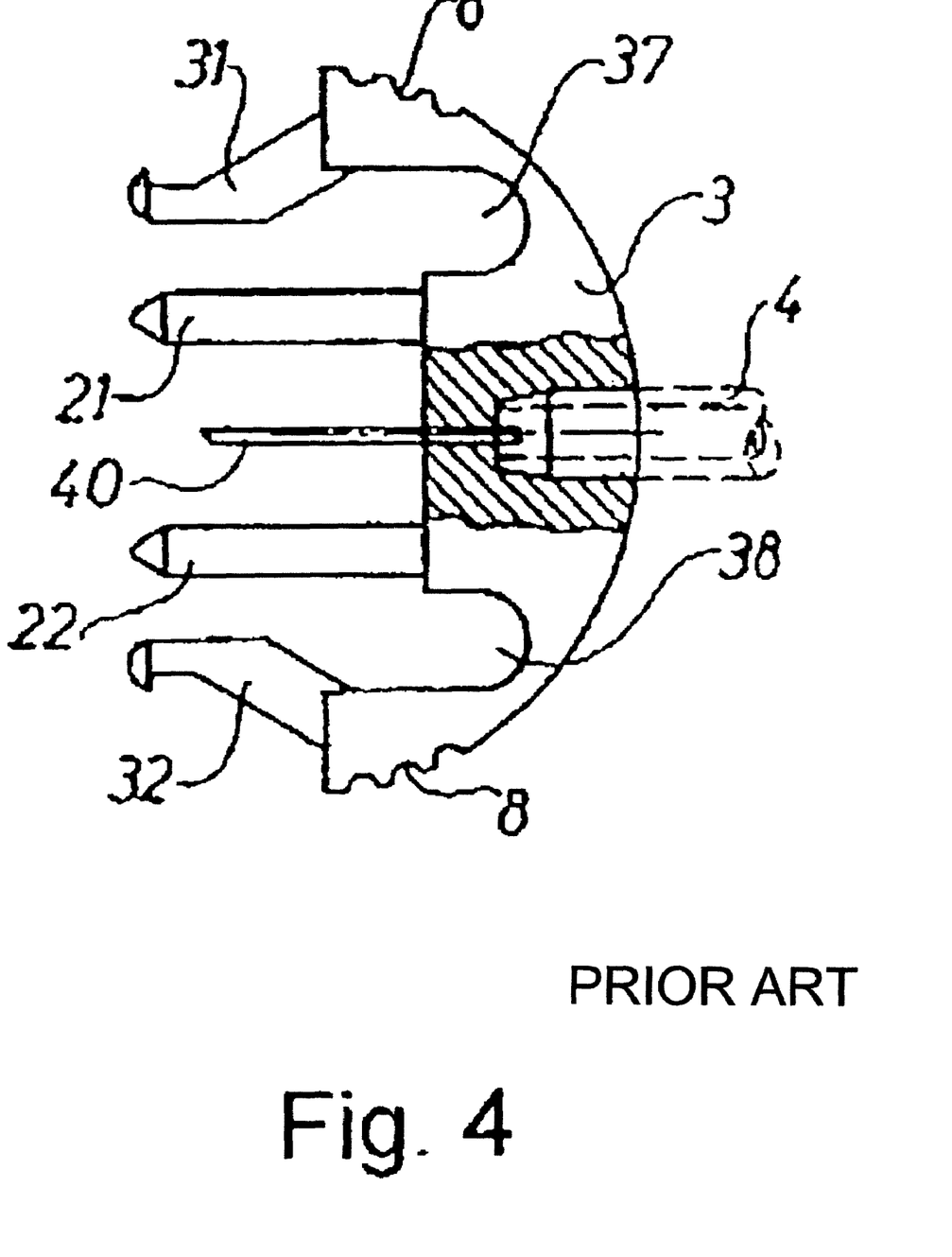

The locking openings 17 and 18 are adapted to receive mating symmetrically shaped locking pins 31 and 32 on the connecting hub 3. As illustrated in FIG. 4, these locking pins 31 and 32 are engaging with the locking openings 17 and 18.

As illustrated in FIG. 2, curve-shaped recesses 37 and 38 are shaped on each side of the locking pins 21 and 22. These recesses ensure that the locking pins 31 and 32 can be moved easily by means of a finger.

FIG. 4 shows furthermore that centrally the connecting hub 3 comprises a needle 40. When inserted through a membrane in the cannula housing 1, this needle provides a connection between the hose 4 of the infusion set and the through passageway 13 of the cannula housing 1.

Figure 5:
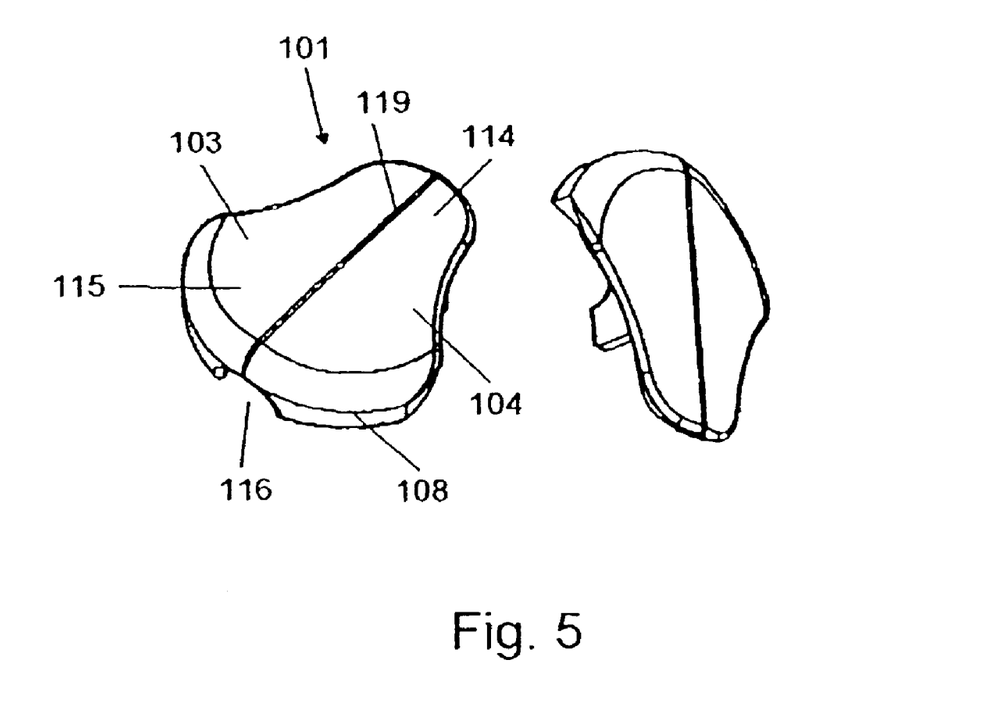
FIG. 5 shows a first exemplary embodiment of a cover according to the invention, seen in a perspective view from above.

Reference now being made to FIGS. 5-9, the cover 101 will be described in further detail. FIG. 5 shows a first exemplary embodiment of a cover 101 seen from the top and comprising an upper plate portion 103 which is shaped to be essentially planar and has an upper face 104 which is plane and smooth. In this case, the upper plate portion 103 is configured as a partially circular element 115 that extends into a tongue part 114. At the delimiting edge of the plate element corresponding to the partially circular area, it extends into a flange 108, wherein flange and plate element form an essentially 90° wide angle—a first angle—to each other. Furthermore, this angle has a partially circular recess 116 essentially corresponding to the centre axis of the cover and arranged symmetrically thereabout, said recess 116 ensuring that hoses can freely and unimpededly extend from whatever infusion device shielded by the cover. Thus the cover is configured symmetrically about its longitudinally extending centre axis 119. Typically the upper plate portion 103 will have a thickness within the range 1.5-2 mm. Typically the flange will assume approximately the same thickness, however, optionally thicker in the transition area between plate and flange.

Figure 6:
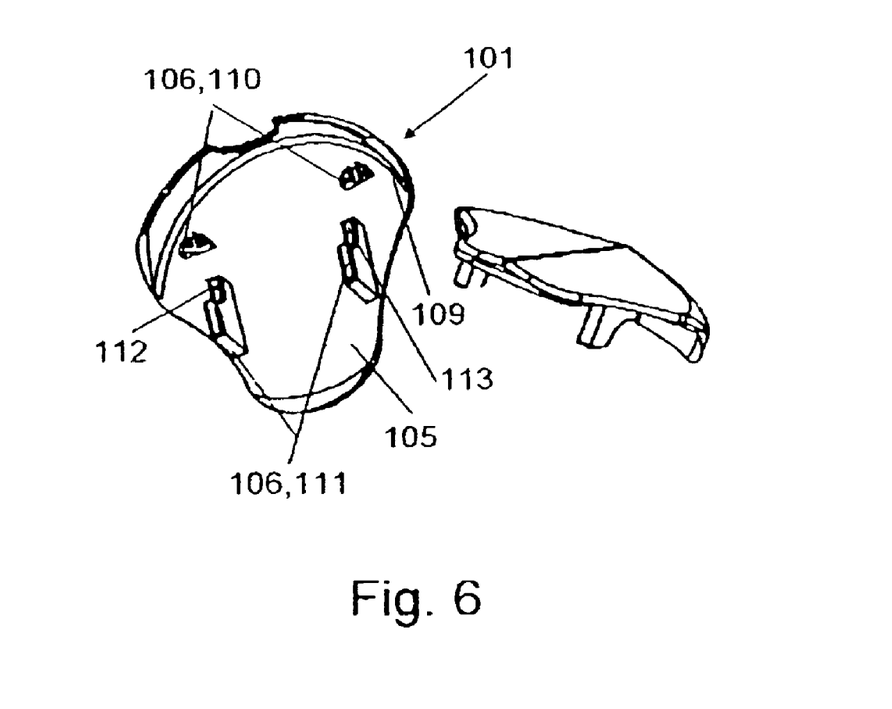
FIG. 6 shows the cover shown in FIG. 5, in a perspective view seen from below.

FIG. 6 shows the cover shown in FIG. 5, seen from below, from where the lower face 105 of the plate element 103 will appear which is essentially plane, optionally slightly curved; such, however, that this face is congruent with the infusion device on top of which it is to be located. This face comprises attachment means 106 that comprise in this case two types, viz two plate elements 111 and two partially cylindrical elements 110. The two plate elements 111 are each configured as rectangular plate elements that are cast integrally with the cover and are located perpendicular to the lower face 105. The rectangular faces of the plate elements are in parallel with the centre axis 114 of the cover and are located with a second mutual spacing, corresponding to 9-10 mm. The plate elements are located in such a manner that, when the cover is located on an infusion device, they will fit into recesses on the infusion device, eg the recesses indicated in FIG. 2 by 37 and 38. Hereby a firm attachment of the cover to the infusion device is ensured, since—on the one hand—there is a span between the two rectangular plate elements and—on the other—a span between flange and plate elements.

Conveniently the plate elements can be provided with a recess: a partially circular recess facing towards the flange and corresponding to the upper free edge, whereby a nail-shaped cavity is provided and being shown in the drawing with a concave face 113 that extends into the side faces at a concave delimiting edge 112. It is the object of this recess to enable the cover to remain in place when the two parts of the infusion device, viz the cannula housing and the connection hub, are separated and wherein the infusion device remains in position on the cannula housing.

Furthermore, in this exemplary embodiment the attachment means 106 also comprise the two partially cylindrical elements 110 that are located with their centre axis perpendicular to the lower face 105 and located at a first mutual distance in such a manner that they fit into the openings and channels on the infusion device 27 and 28 that are shown in FIG. 2. The height of these partially cylindrical attachment means is typically in an order of magnitude of 1 mm. The height of the rectangular plate elements is typically 3.5 mm, whereas the length of the latter is comprised within the range 5-6 mm.

Figure 7:
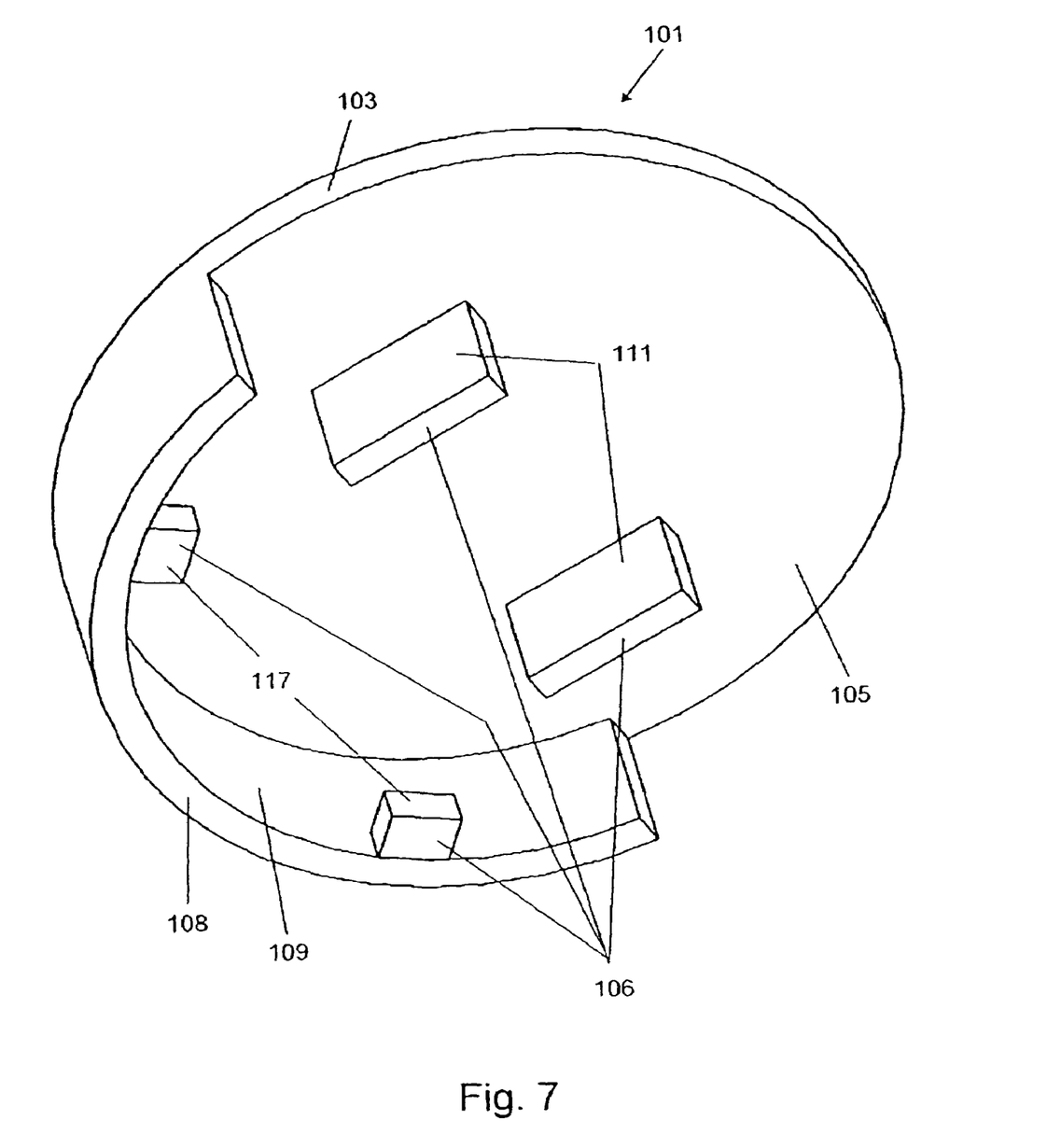
FIG. 7 shows an alternative embodiment according to the invention, seen in perspective view from the bottom.

FIG. 7 shows a further exemplary embodiment of a cover 101 and wherein the difference over those described in FIGS. 5 and 6 resides in the shape of the attachment means and also the geometrical shape of the upper plate part 103. In this case the upper plate element 103 is shaped to be circular and, likewise, the flange is not provided with a recess 116. The rectangular face elements are provided on the same location relative to the infusion device as in FIGS. 5-6, but they do not comprise the concave delimiting edge 112, but constitute a true rectangular plate.

Further attachment means are in this case located on the flange, the inner face 109 of the flange being provided with two blocks 117, whose upper and lower delimiting faces are essentially in parallel with the lower face 105 of the upper plate portion 103. These blocks are able to engage either underneath the lower edge of the infusion device or in suitable recesses on the side faces of the infusion device as such.

Figure 8:
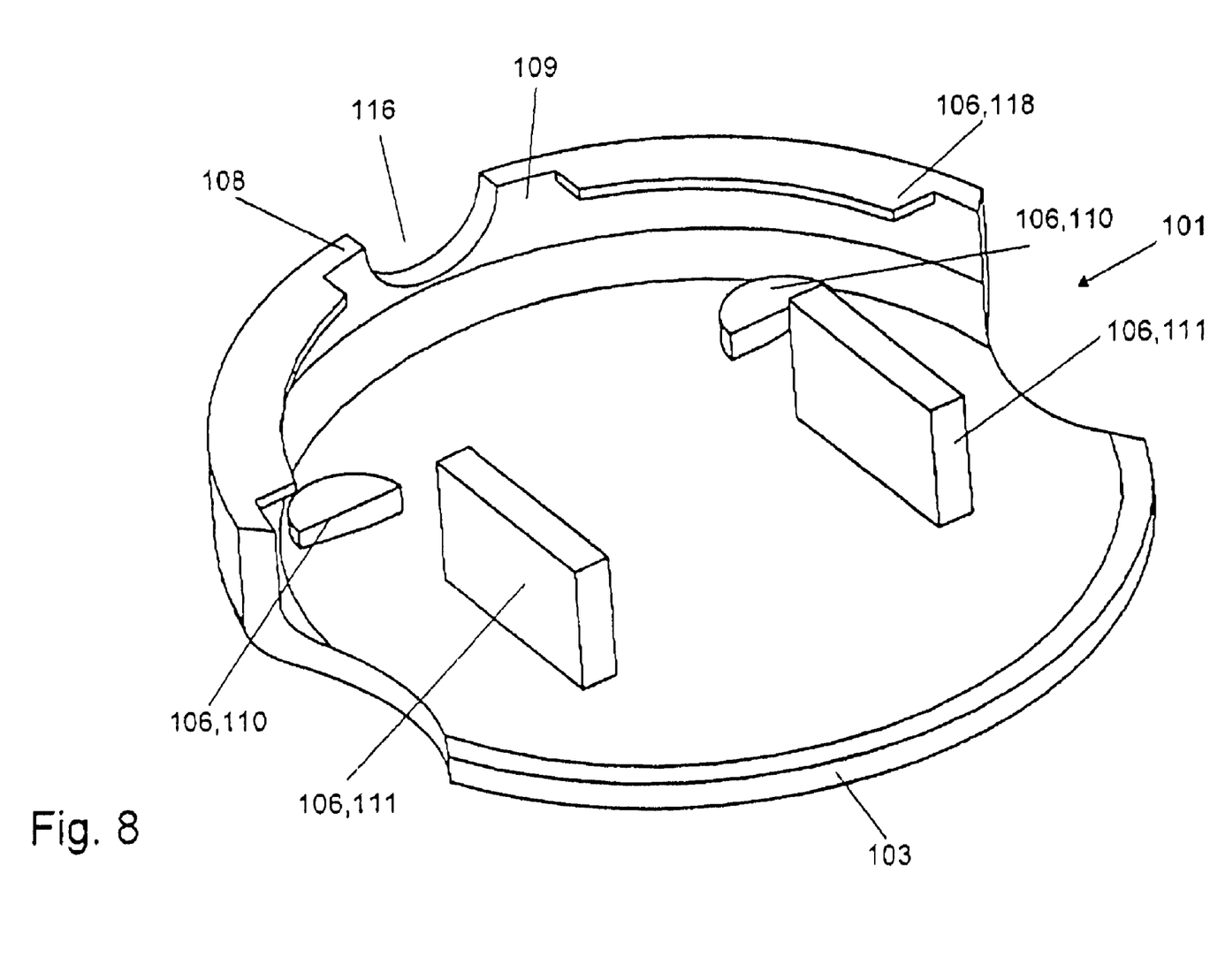
FIG. 8 shows a third exemplary embodiment in accordance with the invention, seen in perspective view and from the bottom.

FIG. 8 shows a third exemplary embodiment of a cover according to the invention showing the attachment means 106 have plate elements 111 that do not include a concave delimiting edge 112. These attachment 106 means are thus true rectangular plates. Furthermore, the flange 108 comprises essentially two wall portions 118 that extend perpendiculary from the flange 108 and has the same material thickness as the flange. the circular recess 116 is provided, between the wall portions 118 and may, engage either in convenient recesses on the infusion device or underneath this lower face. Furthermore the geometrical shape of the upper plate element is not completely circular; recesses having been provided that enable the fingers to more easily seize around the cover.

Figure 9:
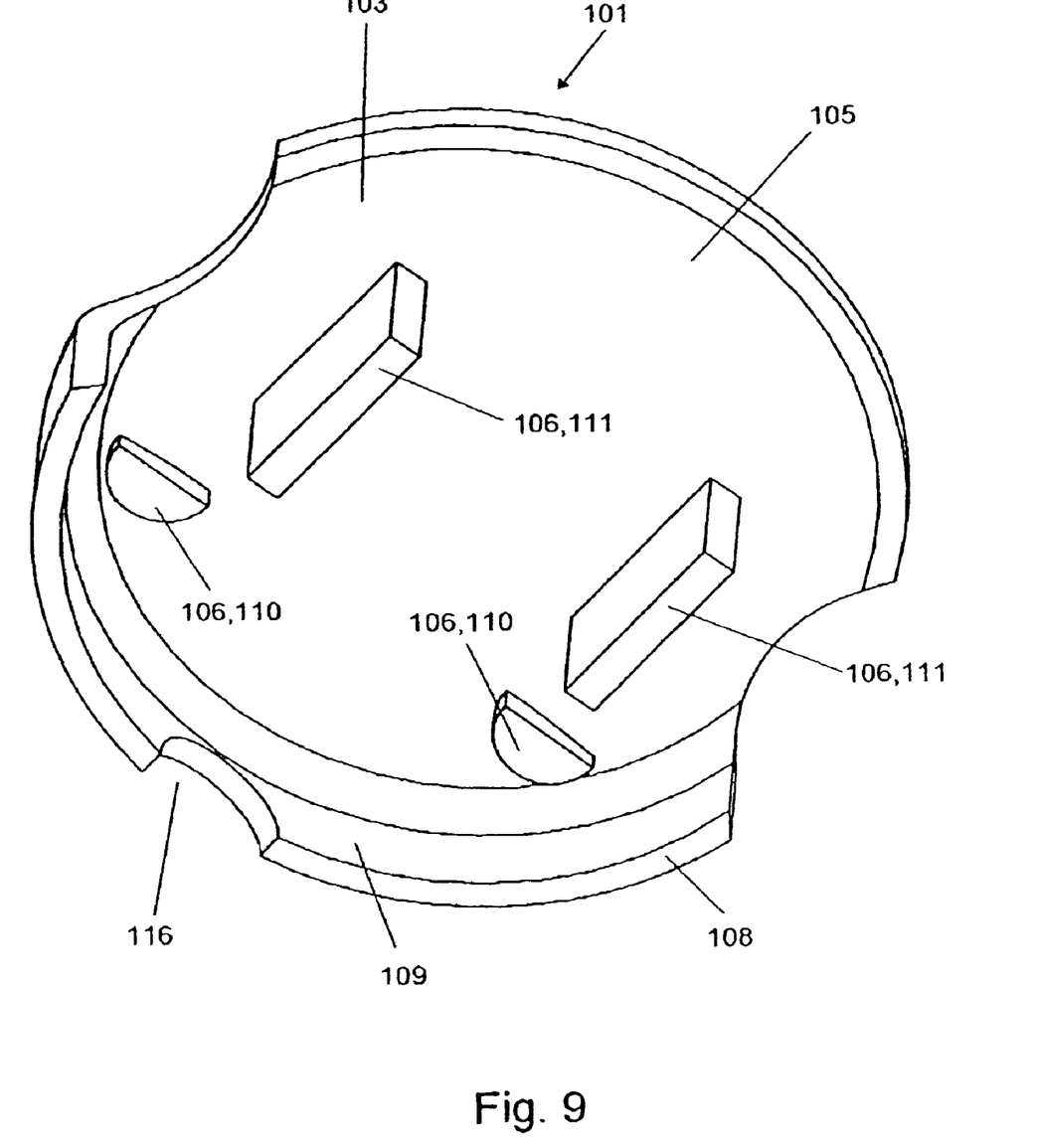
FIG. 9 shows a fourth exemplary embodiment, seen in perspective view and from the bottom.

FIG. 9 is essentially identical to the one shown in FIG. 8, but wherein the perpendicular 118 extending from the flange 108 is not provided.

Conveniently the cover is made in an injection moulding process and wherein suitable materials are M-ABS and PC-ABS.

Figure 10:
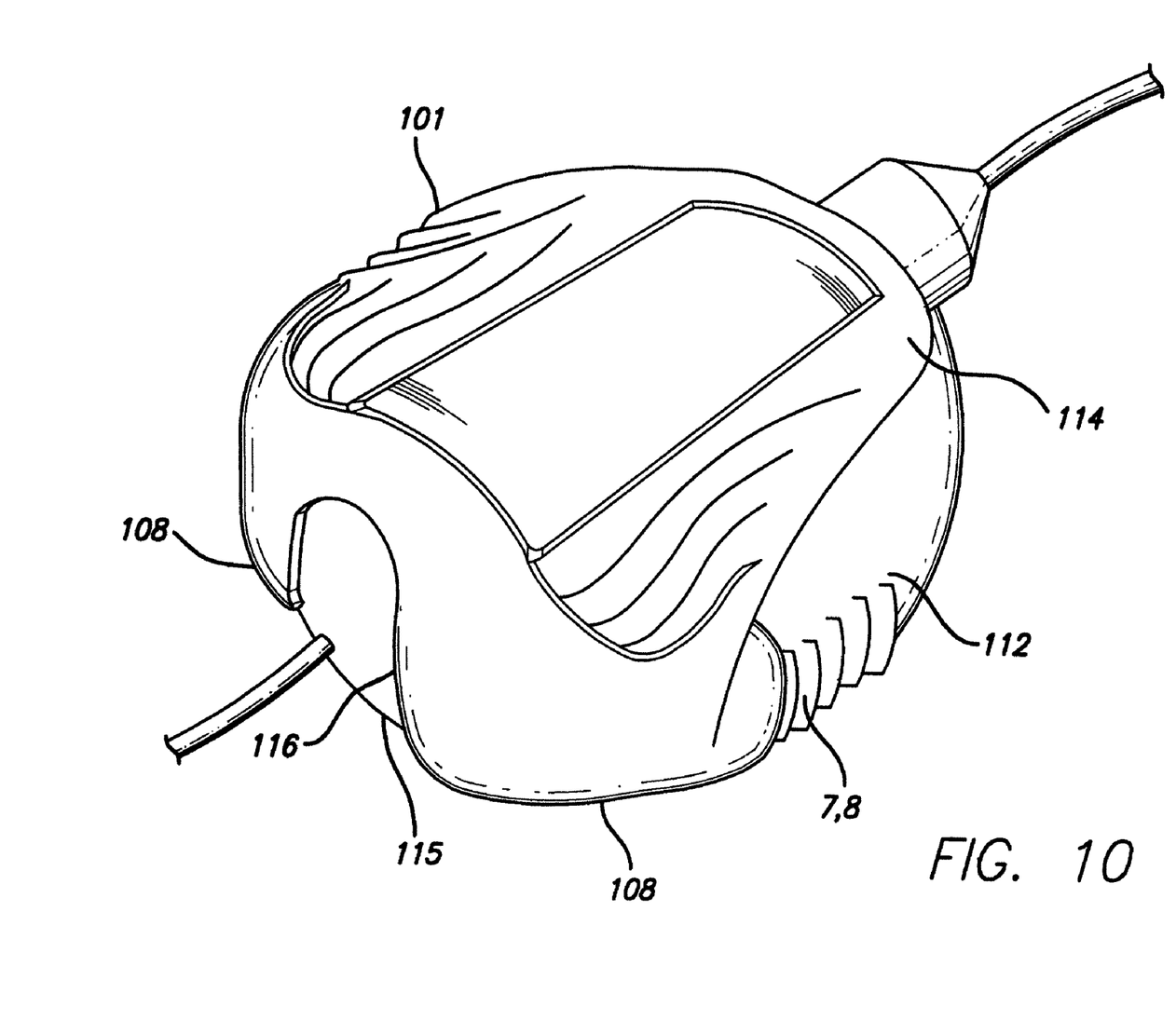
FIG. 10 shows the cover shown in FIG. 5 located on an infusion set in accordance with FIG. 1.

FIG. 10 shows a cover essentially like the one shown in FIGS. 5-6 located on an infusion device corresponding to an infusion device as taught in FIGS. 1-4. Thus the cover is shown to cover any recesses and cut-outs present in the upper face of the infusion device, and wherein the flange 108 engages downwards around the rear side face of the infusion device and corresponding to the rearmost face of the cannula housing and with a circular recess 116 that ensures free access of the hose from the infusion device. When the infusion device is thus to be used, its recesses 7 and 8 are seized and wherein the fingers are pressed towards each other on each their side. By this process the cannula housing and the connection hub are separated from each other. Due to the shape of the cover and the engagement of the attachment means in relation to the infusion device, it remains in place on the cannula housing, while the connection hub is separated off. Subsequently the infusion device can be used as is also taught in eg U.S. Pat. No. 5,522,803.

The cover is not intended for use merely in connection with such infusion device; of course, it may also lend itself to other geometries, wherein the essential aspect is thus that the lower face of the cover has attachment means that engage with elements on the upper face of the infusion device, typically by male/female engagement functionality, wherein the male part is located on the lower face of the cover and wherein the female part are the recesses and other cut-outs that are typically present on the upper face of an infusion device. Whether the upper face of the infusion device is curved or concave, flat or triangular is of lesser relevance, the cover being essentially manufactured with a plate element which is congruent with the face and thus covers the same completely or partially.

The invention claimed is:
1. An infusion device and cover combination, said device for mounting on the skin of a patient, said combination comprising:
    an infusion device including a cannula housing, the housing having a bottom surface configured for placement against the skin and a top surface;
    at least one cannula extending from said cannula housing; and
    a connector hub, said connector hub being releasably connectable with said cannula housing while said cannula housing remains placed against the skin, at least one of said connector hub and said top surface defining at least one recess opening; and
    a cover configured for removable mounting on said infusion device while the patient wears said infusion device, without interfering with the placement of said infusion device on a patient's skin, wherein said connector hub is releasably connectable with said cannula housing while said cover is mounted on said infusion device, said cover comprising:
        a plate element defining at least one protrusion extending therefrom, said protrusion adapted for removable insertion into said at least one recess opening wherein said bottom surface remains free of any protrusions extending from said cover through said bottom surface when said cover is mounted on said infusion device; and
        wherein said plate element further comprises an upper face and a lower face, said at least one protrusion extending from said lower face of said plate element and said lower face of said plate element being oriented towards and substantially congruent with an upper face of said infusion device; and
    wherein said plate element further comprises a relatively thin cross-section in relation to said infusion device, said cross-section being taken through a plane substantially perpendicular to said upper face of said plate element.

2. The infusion device and cover combination of claim 1 wherein said protrusion removably attaches to said cannula housing.

3. The infusion device and cover combination of claim 1 wherein said protrusion removably attaches to said connector hub.

4. Te infusion device and cover combination of claim 1 wherein said cover comprises a plurality of protrusions removably attachable to said infusion device.

5. The infusion device and cover combination of claim 1 wherein said at least one recess opening is located on a top face of said infusion device.

6. An infusion device and cover combination comprising:
    an infusion device including a cannula housing for mounting on the skin of a patient;
    at least one cannula extending from said cannula housing for insertion into the skin of said patient; and
    a connector hub, said connector hub being releasably connectable with said cannula housing while said cannula housing remains mounted on the skin of the patient, at least one of said connector hub and said cannula housing defining at least one recess opening on an upper surface of said infusion device; and
    a cover configured for removable mounting on said infusion device while the patient wears said infusion device, wherein said connector hub is releasably connectable with said cannula housing while said cover is mounted on said infusion device, said cover comprising:
    a plate element having an upper face configured for orientation away from a patient's skin and a lower face facing toward said upper surface of said infusion device, said lower face defining at least one protrusion extending therefrom, said at least one protrusion adapted for removable insertion into said at least one recess opening on said infusion device when said cover is mounted to said infusion device and said cannula is inserted into the skin of said patient;
    said plate element further having a relatively thin cross-section in relation to said infusion device, wherein said cross-section is taken through a plane substantially perpendicular to said upper face of said plate element.

7. The infusion device and cover combination of claim 1 wherein said at least one protrusion further comprises a pair of protruding plate elements.

8. A cover, suitable for being detachably mounted on an infusion device of the kind comprising a cannula housing, at least one cannula extending from said cannula housing for insertion into the skin of a patient, and a connector hub which is releasably connectable with said cannula housing when said cannula housing is mounted on the skin, said cover configured for removably mounting on said infusion device without contacting said cannula when inserted into the skin of the patient, and wherein said connector hub is releasably connectable with said cannula housing while said cover is mounted on said infusion device, said cover comprising an upper plate element having an upper face and a lower face, said plate element having a relatively thin cross-section in relation to the infusion device, said cross-section being taken through a plane substantially perpendicular to said upper face of said plate element, and said lower face of said cover being oriented towards an upper face of said infusion device when said cover is mounted on said infusion device, wherein the lower face of the plate element comprises integrally molded attachment means, said attachment means cooperating with elements of the cannula housing or the connector hub of the infusion device when said cover is mounted on said infusion device and wherein said attachment means do not extend through a bottom surface of the infusion device when said attachment means are fully inserted into said infusion device.

9. The cover according to claim 8, wherein the cover further comprises a flange that forms a first angle in relation to the upper plate and is connected thereto.

10. The cover according to claim 9, wherein a face of the flange facing towards outer side faces of the infusion device is congruent therewith.

11. The cover according to claim 9, wherein an expanse of the upper plate element is smaller than an expanse of an upper face of the infusion device, and wherein the flange extends partially around side faces of the infusion device.

12. The cover according to claim 8, wherein the attachment means are male parts.

13. The cover according to claim 8, wherein the attachment means further comprise at least two protruding partially cylindrical elements located at a first mutual distance.

14. The cover according to claim 8 wherein the attachment means further comprise at least two protruding plate elements located at a second mutual distance.

15. The cover according to claim 14, wherein the protruding plate elements comprise rectangular plate-shaped elements, said rectangular elements extending perpendicularly to said lower face.

16. The cover according to claim 14, wherein each of the protruding plate elements further comprises a concave delimiting edge and concave side face.

17. The cover according to claim 8, wherein the cover covers at least partially a connection between the cannula housing and the connector hub of the infusion device.

18. The cover according to claim 8, wherein the attachment means cooperate with elements on the cannula housing.

19. The cover according to claim 8, wherein the attachment means cooperate with elements of the cannula housing and the connector hub of the infusion device when the cover is mounted on the infusion device.

20. The infusion device and cover combination of claim 6, wherein said at least one recess opening further comprises at least a pair of openings formed by both said connector hub and said cannula housing.

21. The infusion device and cover combination of claim 6, wherein said cover is congruent with said upper face of said infusion set.

* * * * *

UNITED STATES PATENT AND TRADEMARK OFFICE
CERTIFICATE OF CORRECTION

| | |
|---|---|
| PATENT NO. | : 7,481,794 B2 |
| APPLICATION NO. | : 11/223467 |
| DATED | : January 27, 2009 |
| INVENTOR(S) | : Søren Jensen |

It is certified that error appears in the above-identified patent and that said Letters Patent is hereby corrected as shown below:

In column 6, claim 4, line 31, before "infusion device and cover" delete "Te" and substitute --The-- in its place.

Signed and Sealed this

Thirtieth Day of June, 2009

JOHN DOLL
*Acting Director of the United States Patent and Trademark Office*